(12) United States Patent
Theilhaber et al.

(10) Patent No.: US 6,502,039 B1
(45) Date of Patent: Dec. 31, 2002

(54) MATHEMATICAL ANALYSIS FOR THE ESTIMATION OF CHANGES IN THE LEVEL OF GENE EXPRESSION

(75) Inventors: Joachim Theilhaber, Cambridge; Steven Bushnell, Medfield; Rainer Fuchs, Sudbury, all of MA (US)

(73) Assignee: Aventis Pharmaceuticals, Bridgewater, NJ (US)

( * ) Notice: Subject to any disclaimer, the term of this patent is extended or adjusted under 35 U.S.C. 154(b) by 0 days.

(21) Appl. No.: 09/577,634

(22) Filed: May 24, 2000

Related U.S. Application Data
(60) Provisional application No. 60/135,853, filed on May 25, 2000.

(51) Int. Cl.[7] .......................... G01N 33/48; C12Q 1/68
(52) U.S. Cl. ............................................. 702/19; 435/6
(58) Field of Search ................................ 435/6; 702/19

(56) References Cited

U.S. PATENT DOCUMENTS

| | | | |
|---|---|---|---|
| 5,445,934 A | 8/1995 | Fodor et al. | 435/6 |
| 5,800,992 A | 9/1998 | Foder et al. | 435/6 |
| 6,203,987 B1 * | 3/2001 | Friend et al. | 435/6 |
| 6,221,592 B1 * | 4/2001 | Schwartz et al. | 435/6 |

OTHER PUBLICATIONS

Boguski and Schuler, Nat. Genetics 10: 369–371 (1995).
DeRisi et al., Nat. Genetics 14: 457–460 (1996).
Schena et al. Proc. Natl. Acad. Sci. USA 93: 10614–10619 (1996).
Chen et al. J. Biomed. Optics vol. 2 No. 4 pp. 364–374 (1997).

* cited by examiner

*Primary Examiner*—Ardin H. Marschel
*Assistant Examiner*—Monika Sheinberg
(74) *Attorney, Agent, or Firm*—Mintz, Levin, Cohn, Ferris, Glovsky and Popeo, P.C.

(57) ABSTRACT

The present invention relates to a highly accurate and reproducible mathematically-based methodology for quantifying the levels of differential gene expression from microassay protocols. Specifically, the present invention provides a simple deductive approach, grounded in a Bayesian framework, to circumvent the heuristic-based limitation of previous methodologies. Rather than seeking a point-estimate of the fold-change of the level of gene expression, the present invention utilizes the derivation of mathematical formula to determine the a posteriori distribution of all the fold-changes of differential gene expression which may be inferred from the given measurements. From this a posteriori distribution the following information may be obtained: (i) an estimator for the fold-change of the level of gene expression; (ii) confidence limits for the fold-change, at any given confidence level; and (iii) a P-value for assessing the statistical significance of change. The present invention also possesses the advantage that fold-change estimates and confidence limits may even be assigned to signal pairs where both signals are zero or negative, without resorting to heuristic thresholds.

12 Claims, 8 Drawing Sheets

$$\begin{pmatrix} x_1 & x_2 & R_p & R & R_{1-p} & \text{P-VALUE} \\ 100 & 400 & 3.3 & 4.0 & 5.0 & 0.0 \\ 50 & 200 & 2.8 & 3.9 & 6.5 & 5.98 \times 10 \\ 25 & 100 & 2.0 & 3.6 & 8.8 & 4.4J \times 10 \\ 10 & 40 & 0.93 & 2.2 & 7.3 & 0.18 \\ 5 & 20 & 0.51 & 1.5 & 5.'\sim & 0.34 \\ 1 & 4 & 0.32 & 1.1 & 4.6 & 0.46 \\ 0 & 0 & 0.23 & 1.0 & 4.4 & 0.5 \end{pmatrix}$$

Fig. 4

| DECISION PARAMETERS | | RESULTS FOR CONSTANT F.P. RATE $P(0/p) = 0.3$ | | | | |
|---|---|---|---|---|---|---|
| MAIN STATISTIC t | REGION | $N_{TOT}$ | $N_{TP}$ | T.P. RATE $P_{(p/1)}$ | $t_e$ | $\text{Med}(\hat{R})$ |
| FOLD-CHANGE $R$ | $R \geq t_e$ | 371 | 260 | 0.26 | 4.37 | 6.1 |
| P-VALUE $P$ | $P \leq t_e,$ $\hat{R} \geq 1$ | 814 | 570 | 0.57 | 0.037 | 4.2 |
| DISCRIMINANT $\log(\hat{R}) - 5.48P$ | $t \geq t_e$ | 713 | 499 | 0.50 | 0.95 | 4.4 |

Fig. 5

MATHEMATICAL ANALYSIS FOR THE ESTIMATION OF CHANGES IN THE LEVEL OF GENE EXPRESSION

RELATED APPLICATIONS

This application claims priority to U.S. Ser. No. 60/135,853, filed May 25, 2000. The contents of this application are incorporated by reference in their entirety.

FIELD OF THE INVENTION

The present invention relates to a mathematical analysis for the quantitative estimation of the level of differential gene expression. More specifically, the present invention relates to the mathematical derivation of an a posteriori distribution of all the fold-changes of the level of gene expression which may be inferred from the given experimental measurements.

BACKGROUND OF THE INVENTION

Cells rely upon their numerous protein components for a wide variety of functions. These functions include, e.g., the production of energy, the biosynthesis of all component macromolecules, the maintenance of cellular architecture, the ability to act upon intra- and extracellular stimuli, and the like. Each cell within an organism in contains the information necessary to produce the repertoire of proteins that organism can expressed. This information is stored as genes within the organism's genome. The number of unique human genes is estimated to be 30,000 to 100,000.

For any given cell, only a portion of the gene set is expressed in the form of protein. Some of the proteins are likely to be present in all cells (i.e., are ubiquitously expressed) because they serve biological function(s) which are required in every type of cell, and can be thought of as "housekeeping" proteins. In contrast, other proteins serve specialized functions that are only required in particular cell types. For example, muscle cells contain specialized proteins that form the dense contractile fibers of a muscle. Given that a large part of a cell's specific functionality is determined by the genes it is expressing, it is logical that transcription, the first step in the process of converting the genetic information stored in an organism's genome into protein, would be highly regulated by the control network that coordinates and directs cellular activity.

Regulation of gene expression is readily observed in studies that examine activities evident in cells configuring themselves for a particular function (e.g., specialization into a muscle cell) or state (e.g., active multiplication or quiescence). Hence, as cells alter their status, the coordinated transcription of the protein(s) which are requited for this molecular biological/physiological "state" can be observed. This highly detailed, global knowledge of the cell's transcriptional state provides information on the cell's status, as well as on the biological system(s) controlling this status. For example, knowledge of when and in what types of cell the protein product of a gene of unknown function is expressed would provide useful clues as to the likely function of that gene. Determination of gene expression patterns in normal cells could provide detailed knowledge of the way in which the control system achieves the highly coordinated activation and deactivation required for development and differentiation of a mature organism from a single fertilized egg. Comparison of gene expression patterns in normal and pathological cells could provide useful diagnostic "fingerprints" and help identify aberrant functions that would be reasonable targets for therapeutic intervention.

Unfortunately, the ability to carry out studies in which the transcriptional state of a large number of genes is determined has, until recently, been inhibited by limitations on the ability to survey cells for the presence and abundance of a large number of gene transcripts in a single experiment. One limitation can be in the small number of identified genes. In the case of humans, only a few thousand proteins encoded within the human genome have been physically purified and quantitatively characterized to any extent. Another limitation can be in the manner of transcription analysis.

Two recent technological advances address have aided analyses of gene transcription. The cloning of molecules derived from mRNA transcripts in particular tissues, followed by the application of high-throughput sequencing to the DNA ends of the members of these libraries has yielded a catalog of expressed sequence tags (ESTs). See e.g., Boguski and Schuler, Nat. Genetics 10: 369–370 (1995). These "signature sequences" can provide unambiguous identifiers for a large cohort of genes.

In addition, the clones from which these sequences were derived provide analytical reagents that can be used in the quantitation of transcripts front biological samples. The nucleic acid polymers, DNA and RNA, are biologically synthesized in a copying reaction in which one polymer serves as a template for the synthesis of an opposing strand, which is termed its complement. Following the separation of the strands from one another (i.e., denaturation), these strands can be induced to pair, quite specifically, with other nucleic acid strands possessing a complementary sequence in a process called hybridization. This specific binding can be the basis of analytical procedures for measuring the amount of a particular species of nucleic acid, such as the mRNA specifying a particular protein gene product.

A second advance involves microarray/microassay technology. This is a hybridization-based process which allows simultaneous quantitation of many nucleic acid species. See e.g., DeRisi et al., Nat. Genetics 14: 457–460 (1996); Schena et al., Proc. Natl. Acad. Sci. USA 93: 10614–10619 (1996). This technique combines robotic placement (i.e., spotting) of small amounts of individual, pure nucleic acid species on a glass surface, hybridization to this array with multiple fluorescently-labeled nucleic acids, and detection and quantitation of the resulting fluorescent-labeled hybrids with, for example, a scanning confocal microscope. When used to detect transcripts, a particular RNA transcript (i.e., an mRNA) can be copied into DNA (i e., a cDNA) and this copied form of the transcript is subsequently immobilized onto, for example, a glass surface.

A problem in the analysis of gene expression data is the estimation of the overall fold-change in the expression level of a gene in one experiment relative to its expression in another experiment. Given these two raw measurements of the fold-change in gene expression level, the simplest approach, as utilized by previous methodologies, has been to take the arithmetic ratio of the values as an estimate of the overall fold-change. While for very strong signals this leads to a meaningful estimate of the fold-change in the underlying mRNA concentrations, for weaker signals the results are much more ambiguous because of contamination by the "noise" which is indigenous to the particular experimental system utilized. Another previously utilized technology for the estimation of the fold-change in gene expression level is based upon differential-signal intensities (e.g., the Affymetrix® chip). However, the values assigned to expression levels by use of the aforementioned methodology can be negative, thus leading to the awkward situation of negative or undefined gene expression ratios.

SUMMARY OF THE INVENTION

The present invention provides a highly accurate and reproducible mathematically-based methodology for quantifying the levels of differential gene expression from microassay protocols.

The methods of the present invention can be used to calculate differences in the level of gene expression in one or more arrays of genes. The methods involve defining the experimental noise associated with intensity of hybridization signal for each gene in the array(s). The experimental noise is variations in observed levels on chips or other microarrays rather than biological noise, which is the variation of expression level seen in biological systems. Detection of genes is often, but not always, based on fluorescence. Other detection systems have been used which may be adapted here. Such systems include luminescent or radioactive labels, biotinylated, haptenated, or other chemical tags that allow for easy detection of labeled probes.

For a mathematical description, see Section I—Formulation of the Noise Model below. The noise is assumed to be Gaussian and Bayes Theorem is applied. The defined experimental noise term, sigma, is then used to define an analytical (i.e., analytical in the mathematical sense meaning that it is a continuous function) probability distribution function ("pdf") describing distribution values of intensity for each gene. These pdfs are used to derive an analytical joint pdf describing possible ratios or fold changes for any differentially-expressed gene or gene product in the array(s). The joint pdfs are applied using experimentally-derived intensities and noise values from the genes on the array(s) (1) to estimate fold changes in the concentration of gene transcripts, (2) to use the jpdf to establish the confidence limits on the fold change given specific confidence intervals, and (3) to derive a p-value, or quality metric (the probability a fold change could be less than 1, when the estimate is greater than 1, or, the probability that the fold change is greater than 1, when the estimate is less than 1), associated with the fold change estimate. The estimated fold change determined by the methods of the present invention represents the difference in level of gene expression observed. The total variance (i.e., noise) may still be high even as the concentration of transcript goes to zero. The methods of the present invention use a mathematical formula to describe an a posteriori statistical distribution of all the levels of gene expression which may be derived from the measurements obtained of levels of gene expression in one or more cells or tissue types represented in the array(s).

Microarrays are an ordered array of double stranded or single stranded DNA molecules positioned on a support material in a spatially separated organization. In contrast to filter "macroarrays", which are typically large sheets of nitrocellulose, microarrays position the DNA more densely packed organization such that up to 10000 DNA molecules can be fit into a region typically 1–4 square centimeters. Microarrays typically use coated glass as the solid support, in contrast to the nitrocellulose-based material of filter arrays. By having an ordered array of DNA samples, the position of each sample can be tracked and linked to the original sample from which the DNA on the array was generated. Methods and apparatus for preparing a microarray have been described. See, e.g., U.S. Pat. Nos. 5,445,934 and 5,800,992, both incorporated herein by reference.

The DNA samples on the microarray are hybridized with RNA or DNA probes that have been fluorescently labeled to identify whether the probe sample contains a molecule that is similar or identical to the DNA sample on the microarray. Under the appropriate conditions, probe molecules hybridize to a DNA molecule on the microarray. Generally, identical or near identical sequences form productive hybrids. The presence of DNA-probe hybrid molecules is detected by a fluorescence detection instrument. If the hybridization signal is weak or non-existent at a particular DNA site, then the corresponding DNA or RNA molecule in the probe is absent. Current microarray instruments can hybridize up to four different fluorescent probe samples at one time. With improvements to the technology, more probes can be hybridized at once.

Up until recently, DNA hybridizations were performed on nitrocellulose filters. In contrast to microarrays where DNA is spotted directly onto the microarray, filter arrays are generated by spotting bacterial colonies on the filters, placing the filters over a agar growth media, and incubating the filters under conditions that promote the bacterial colonies to grow. The DNA within the bacterial colonies is released by lysing the colony and treating the filters to fix the DNA to the filter material. The process of generating a bacterial filter array can take typically 2–4 days. Microarrays have a number of advantages over filter array methods. For example, filter methods generally array bacterial colonies in which the cloned cDNA is contained. The colonies must be grown up over several days, lysed to release DNA and fix DNA onto the filter. Hybridization to filter arrays of colonies is less reliable due to bacterial debris and the low amount of DNA released from the colony. A second advantage is that the iterations are quicker with microarrays than with filters. This is due to the time needed to grow colonies on the filters and prepare them for the next round of hybridization. In contrast, probing of a subsequent microarray can begin less than 24 hr after analysis of an array is completed. Another advantage of microarrays is the ability to use fluorescently labeled probes. This provides for a non-radioactive method for hybridization detection. In contrast, filter hybridization generally uses probes labeled with radioactive phosphorus or sulfur. Microarrays can be hybridized with multiple probes simultaneously. In contrast, filter arrays can only be hybridized with one probe at a time. One of the most important advantages of microarrays is their reproducibility and sensitivity of hybridization signals. Typically, hybridization signals are higher and sensitivity is greater on microarrays versus filter arrays. In addition, filter arrays often exhibit spurious background signals that are unrelated to productive hybridization between the probe and DNA on the filter.

Once the random sample of nucleic acid fragments is immobilized to a solid surface (e.g., glass) in a microarray, the random sample of nucleic acid fragments can then be hybridized to one or more labeled probes complementary to genes or sequences of interest. Generally, the unhybridized probes are removed. The labeled probes are then detected by methods known in the art (e.g., confocal microscopy). For example, slide images can be analyzed with Array Vision image analysis software (Imaging Research) for spot finding analysis, localized background determination, distribution of signal intensities in a spot, and signal to noise ratios. Statistical assessment is then performed as described below.

The present invention utilizes a mathematically-based methodology to quantitative the fold-change in the levels of differentially expressed genes. Specifically, the present invention uses a simple deductive approach, grounded in a Bayesian framework, to circumvent the heuristic-based limitation of previous methodologies used in the mathematical analysis of differential gene expression. The present invention, rather than immediately seeking a point-estimate of the fold-change of the level of gene expression, derives a mathematical formula for the a posteriori distribution of all the fold-changes of differential gene expression which may be inferred from the given measurements. From this a posteriori distribution the following information may be obtained: (i) an estimator for the fold-change of the level of gene expression; (ii) confidence limits for the fold-change, at any given confidence level; and (iii) a P-value for assessing the statistical significance of change. An additional advantage of the present invention is that fold-change estimates and confidence limits may even be assigned to signal pairs where both signals are zero or negative, without resorting to heuristic thresholds. Hence, the mathematical framework disclosed herein unifies estimation for all signals within a given sample.

BRIEF DESCRIPTION OF THE DRAWINGS

FIG. 4 illustrates, in tabular form, the results of fold-change estimates R, 68% confidence intervals $(R_p, R_{p-1})$, and P-values for significant positive fold-change, for all the measurement pairs of FIG. 1.

FIG. 5 illustrates, in tabular form, the results of the performance of three statistical methodologies utilized for the detection of 1000 genes with actual fold-change of b=3 against a background of 4000 genes with no change (b=1), based upon Monte Carlo simulations described in Section 6 herein (i.e., the a priori probability of a gene undergoing the 3-fold change is $P_1=0.2$). Specific results are reported for a fixed false positive rate P(0|p)=0.3.

DETAILED DESCRIPTION OF THE INVENTION

Figure 10:
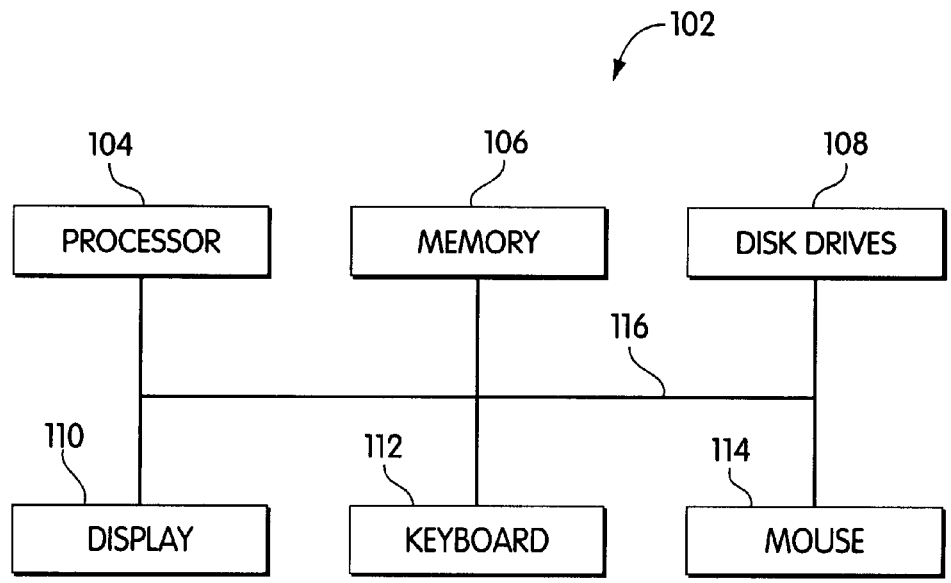
FIG. 10 is a block diagram of a computer system for implementing features of the invention.

Referring to FIG. 10, a computer system 102 includes a processor 104, memory 106, disk drives 108, a display 110, a keyboard 112, and a mouse 114. The processor 104 can be a personal computer central processing unit (CPU) such as a Pentium® III processor made by Intel® Corporation. Memory 106 includes random access memory (RAM) and read-only memory (ROM). The disk drives 108 include a hard-disk drive and can include floppy-disk drives, a CD-ROM drive, and/or a zip drive. The display 110 is a cathode-ray tube (CRT), although other forms of displays are acceptable, e.g., liquid-crystal displays (LCD) including TFT displays. The keyboard 112 and mouse 114 provide data input mechanisms for a user (not shown). The components 104, 106, 108, 110, 112, and 114 are connected by a bus 116. The computer system 102 can store, e.g., in memory 106, software code containing instructions for controlling the processor 102 to perform functions described below.

1. Formulation of the Noise Model

The measurements of the expression level of a given gene, in different or replicated experiments, is based upon x, which can be written:

$$x = Cn + \epsilon, \tag{1}$$

where n is the absolute physical concentration (molarity) of the mRNA of the gene in solution, where C is a proportionality constant linking molarity to recorded intensity, and where $\epsilon$ is a noise term. In the following equations, the determination of the absolute mRNA concentration is not sought and thus, for simplicity, the following value is set C=1:

$$x = n + \epsilon. \tag{2}$$

In Equation (2) the noise term may be decomposed into three separate contributions:

$$\epsilon = \epsilon_b + \epsilon_c + \epsilon_p, \tag{3}$$

where $\epsilon_b$ is a variation arising from fluctuations in background intensity, where $\epsilon_c$ is a term arising from cross-hybridization of other mRNAs (specific or non-specific), and where $\epsilon_p$ is a "proportionate variation" term, which arises from chip-to-chip variations in oligonucleotide or cDNA density, and other similar, factors. For example, with the Affymetrix® chips, where the final signal x is obtained from averaging over several differential signals, each of the noise terms can be positive or negative, with approximately zero average. Accordingly, the background and cross-hybridization terms may be grouped into a single noise term:

$$\epsilon_C = \epsilon_b + \epsilon_c \tag{4}$$

and the mean and variance of the total noise $\epsilon$ are written as:

$$<\epsilon> = 0, \tag{5}$$

$$\sigma_\epsilon^2 = \text{var}(\epsilon_C) + \text{var}(\epsilon_p) = \sigma_C^2 + (an)^2, \tag{6}$$

where $\alpha$ is the proportionate variation parameter, such that $\text{var}(\epsilon p) = \sigma_p^2 = (\alpha n)^2$. The proportionate variation term a is similar to the coefficient of variation c (initially defined by Chen et al., *J. Biomed. Optics* 2: 364 (1997)). Other noise terms intervene in this model as well, so that the total variance of the noise may remain large even as n→0. In the following equations it is assumed that $\epsilon$ is normally distributed.

Utilizing the Affymetrix® chips as an example, the combined background and cross-hybridization noise variance $\sigma_c^2$ are computed by taking the variance of the measurements x for all genes signaled as absent by the absence/presence decision algorithm. The proportionate term has been estimated by comparing the highest quartile of intensities in replication experiments.

To illustrate the magnitude of the terms within Equation (6) for a typical Affymetrix® chip-based experiment the median value of the expression levels x is Med(x)≈80, with $\sigma_c$≈25 and α≈0.25. Thus, the median signal over noise ratio Med(x)/$\sigma_c$ is only approximately 3. The standard deviation of the background noise alone is $\sigma_b$≈3–4, so that $\sigma_b$<<$\sigma_c$ with cross-hybridization noise dominating background noise by almost an order of magnitude.

Because the variable $\sigma_c$ is relatively large, and α is small, Equation(6) can be slightly simplified by writing n≈x on the right-hand side of the equation:

$$\sigma_\epsilon^2 = \sigma_c^2 + (\alpha x)^2, \qquad (7)$$

so that the underlying concentration need not be known beforehand in order to quantitatively estimate the variance of the noise.

2. A Posteriori Distribution of Concentrations

While Equation(2) gives the measurement in terms of the concentration, the invention obtains the concentration as a function of the measurement. This may be formulated in probabilistic terms, by writing Bayes Theorem for the variable n and x:

$$P(n|x) = \frac{P(x|n)P(n)}{P(x)}. \qquad (8)$$

In Equation (8), P(x|n) is the conditional probability distribution function (pdf) for x, conditional on n, P(n) is the a priori distribution of n (thus, reflecting the state of knowledge of n prior to the measurement actually being taken), and P(x), the pdf for x, is essentially a normalization term. Hence, from Equation (2) and with the assumption of Gaussian noise, the following equation may be derived:

$$P(x|n) = \frac{1}{(2\pi\sigma_\epsilon^2)^{1/2}} \exp(-(x-n)^2/2\sigma_\epsilon^2), \qquad (9)$$

wherein $\sigma_\epsilon = \sigma_\epsilon(n)$, Equation (6).

For the distribution P(n), as a priori knowledge, only the fact that the concentration is necessarily non-negative is utilized:

$$P(n) = \begin{cases} 0 & n < 0, \\ \mu^{-1} n^{\mu n}, & n \geq 0, \end{cases} \qquad (10)$$

where the limit $\mu \to 0$ very shortly (this is just an artifice to get a step-function distribution in the limit $\mu \to 0$, while keeping P(n) integrable at all times). Finally, P(x) is obtained by integration:

$$P(x) = \int_{-\infty}^{\infty} dn P(n) P(x|n). \qquad (11)$$

With the limit $\mu \to 0$, Equation (8) may be rewritten in the following manner:

$$P(n|x) = \frac{P(x|n)}{\tilde{P}(x)}, n \geq 0, \qquad (12)$$

where P(x|n) is given by Equation (9) and where the denominator is now:

$$\tilde{P}(x) = \int_0^\infty dn P(x|n). \qquad (13)$$

Equation (13) can be readily evaluated using error functions. Rather than directly explore the consequences of Equation (12) on estimation of concentrations, it will be utilized below to quantify the distribution of fold-changes.

3. A Posteriori Distribution of Fold-Changes

For a given gene, it may be assumed that one wishes to evaluate the fold-change in the level of gene expression between two given experiments (e.g., Experiments 1 and 2). For example, if the mRNA concentrations in the experiments are $n_1$ and $n_2$, respectively, then the fold-change R of the concentration in Experiment 2 relative to Experiment 1, is given by:

$$R = \frac{n_2}{n_1}. \qquad (14)$$

While in Equation (14), there is no direct access to $n_1$ and $n_2$, the estimation of R in Bayesian terms can be immediately formulated by writing the a posteriori distribution of R as:

$$f_R(R|x_1, x_2) = \int_0^\infty dn_1 \int_0^\infty dn_2 \delta\left(\frac{n_2}{n_2} - R\right) P(n_1|x_1) P(n_2|x_2), \qquad (15)$$

where $x_1$ and $x_2$ are the intensity measurements in Experiments 1 and 2, respectively, where δ(...) refers to the Dirac delta function, and where P(n|x) is given in Equation (12) above.

Performing the integration indicated in Equation (15) is a very straightforward, if slightly tedious, task. The distribution function for R (i.e., dropping the explicit dependence on $x_1$ and $x_2$ in $f_R(R|x_1,x_2)$) is obtained by:

$$f_R(R) = \frac{C(x_1)C(x_2)}{2\pi\sigma_1\sigma_2} \exp\left(-\frac{x_1^2(R-R_0)}{2(\sigma_2^2 + R^2\sigma_1^2)}\right) I(x_1, x_2), \qquad (16)$$

where $\sigma_i^2 = \sigma_\epsilon^2(x_i)$, I=1, 2, with $\sigma_\epsilon(x)$ now given by Equation (7), with the normalization term:

$$C(x) = \frac{2}{1 + \text{erf}(x/\sqrt{2}\,\sigma_\epsilon(x))}, \qquad (17)$$

where erf is the error function (see Abramowitz, M. and Stegun, I. A., p. 297 *Handbook of Mathematical Functions* (Dover, New York, 1972)), and with the definition:

$$I = \sigma_{12}^1 \exp\left(-\frac{\alpha_{12}^2}{2\sigma_{12}^2}\right) + \alpha_{12}(2\pi\sigma_{12}^2)^{1/2}\frac{1}{2}(1 + \text{erf}(\alpha_{12}/\sqrt{2}\,\sigma_{12})), \qquad (18)$$

where:

$$\frac{1}{\sigma_{12}^2} = \frac{1}{\sigma_1^2} + \frac{R^2}{\sigma_2^2}, \quad (19)$$

$$\alpha_{12} = \left(\frac{x_1}{\sigma_1^2} + \frac{Rx_2}{\sigma_2^2}\right) \bigg/ \left(\frac{1}{\sigma_1^2} + \frac{R_2}{\sigma_2^2}\right). \quad (20)$$

Although rather complex-looking, Equation(16) possesses only two simple limits which will be discussed below through the utilization of two scenarios.

3.1 Case 1—High Concentrations:

If in both experiments the RNA concentrations are large compared to the standard deviation of the noise, with consequence $x_i \gg \sigma_\epsilon(x_i)$, i=1,2, R possess an approximately normal distribution:

$$f_R(R) \approx \frac{1}{(2\pi\sigma_R^2)^{1/2}} \exp\left(\frac{(R-R_0)^2}{2\sigma_R^2}\right). \quad (21)$$

In this limit, the mean of R is just the ratio of the measurements:

$$\langle R \rangle = R_0 = \frac{x_2}{x_1}. \quad (22)$$

Hence, the variance $\sigma_R^2$ of R is given by:

$$\sigma_R^2 = \frac{\sigma_2^2 + x_2^2 \sigma_1^2 / x_2^2}{x_2^2}. \quad (23)$$

Using Equation (7), in turn, a simple approximation for the standard deviation of R may be obtained:

$$\sigma_R = \sqrt{2}\alpha R_0. \quad (24)$$

Thus, in the high-concentration limit (i.e., Case 1) the standard deviation of actual fold-change relative to the ratio of the measurements is given by a constant:

$$\frac{\sigma_R}{R_0} = \sqrt{2}\,\alpha. \quad (25)$$

Upon examination, Equation (24) indicates that no matter how large the signal(s), there will remain an irreducible variation in fold-change estimation of order $\sqrt{2}\alpha(\approx \pm 35\%$ for $\alpha=0.25$) of the overall fold-change which is to be measured.

3.2 Case 2—Very Low Concentrations:

If in both experiments the RNA concentrations are so low that $x_i \ll \sigma_\epsilon(x_i)$, I=1,2, then the distribution takes on the "universal" form of:

$$f_R(R) \approx \frac{1}{\pi} \frac{1}{1+R^2}. \quad (26)$$

where $\sigma_1=\sigma_2$ is assumed for the sake of simplicity.

In this limit, the distribution of R is completely independent of the concentrations, the influence of which has been overwhelmed by the noise. Equation(26) defines a so-called Cauchy distribution (see e.g., Keeping, E. S., *Introduction to Statistical Inference*, (Dover, N.Y., 1995)), which is very broad and does not have a finite mean. One indigenous "pathological" property of the Cauchy distribution is that the mean of many independent samples does not converge, in any sense, to a single number, but rather remains distributed according to Equation (26), regardless of the total number of samples utilized. Conversely, the median over the Cauchy distribution is exactly 1, and the sample median converges to 1, without any of the aforementioned pathologies associated with the median.

The cumulative distribution function of R is given by:

$$P(R<\rho)=2/\pi \tan^{-1}\rho. \quad (27)$$

For example, the 90% confidence limits are (0.16, 6.3), showing that the distribution of Equation (26) is very broad, since these bounds will obtain even when $R_0=1$, provided that the signal is weak enough when compared to the noise.

Finally, under the transformation $\mu=\log R$, the distribution function of Equation (26) becomes completely symmetrical:

$$f_u(u) = \frac{1}{\pi} \frac{1}{\cosh(u)}. \quad (28)$$

so that a logarithmic representation may be useful in some cases, although additional uses of the transformation shall not be pursued further herein.

Figure 1:
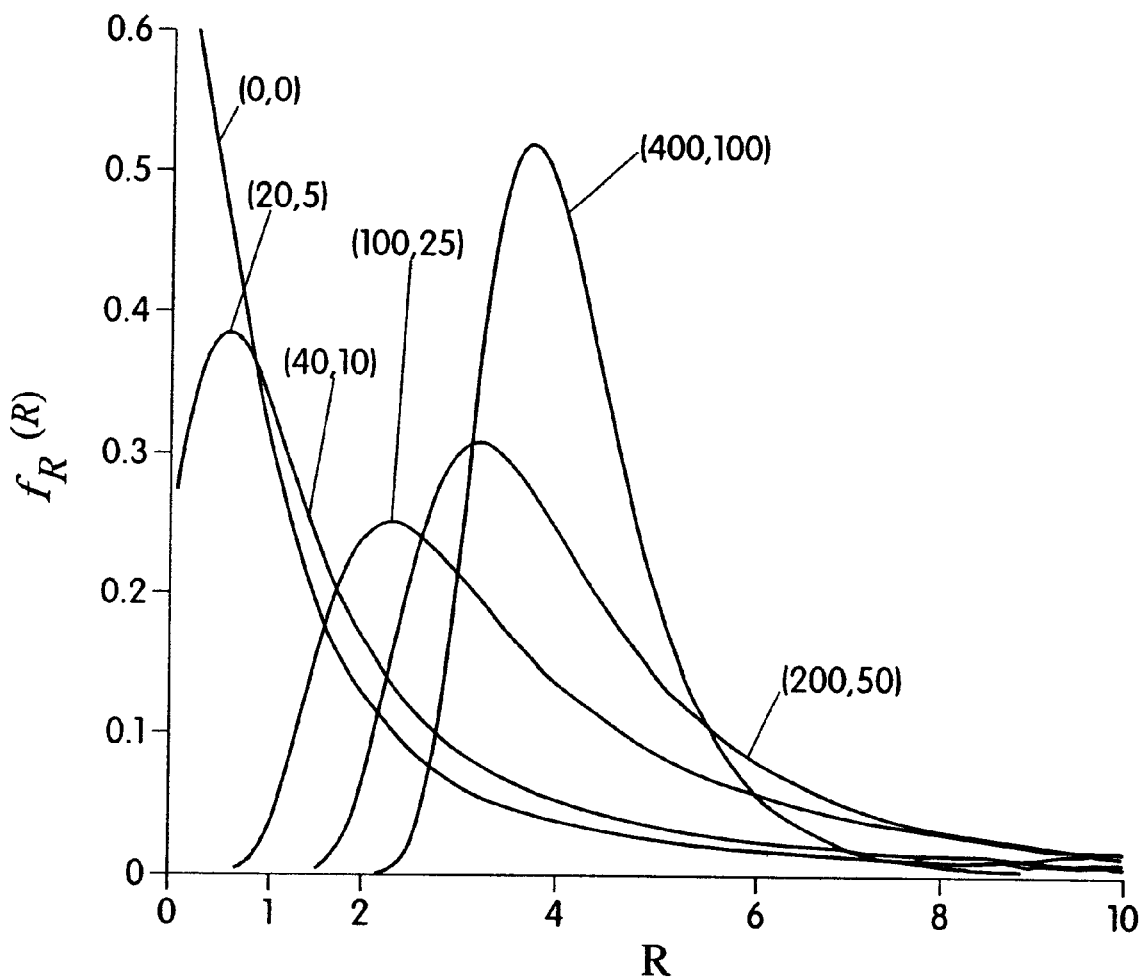
FIG. 1 is a line graph illustrating an a posteriori distribution of the fold change, Equation (16), for a series of measurement pairs $(x_1, x_2)$. In all cases but (0, 0), the ratio of measurements is 4. The standard deviation of both noise terms is kept constant at $\sigma_1=\sigma_2=20$.

FIG. 1 displays the a posteriori distribution $f_R(R)$ for a series of pairs $(x_1, x_2)$, for constant standard deviation of both noise terms $\sigma_1=\sigma_2=20$. In this figure, the ratio $x_2/x_1$ is always 4 (except for the case where both signals are 0), but the signal-to-noise ratio is highly variable. At the very highest signal levels, $(x_1, x_2)=(100,400)$, and $f_R(R)$ is strongly peaked about R=4. Even in this limit, however, visual inspection indicates that the 68% confidence interval (corresponding to a width of two standard deviations for a normal distribution) is roughly (3, 5). This shows that even when the lowest signal-to-noise ratio is 100/20=5, the actual fold-change cannot be inferred to a value better than $3 \leq R \leq 5$.

With decreasing signal-to-noise ratio, the distribution $f_R(R)$ not only broadens, but its peak shifts downwards. Thus, in FIG. 1 for the measurement pair (40, 10), the median of the distribution is about 2.2, with the actual maximum occurring very close to a value of 1. This broadening and shifting of the distribution function indicates that for weakening signals, the ratio of the measurements becomes an increasingly less reliable indication of the actual fold-change. Finally, in the limit of measured values both zero, (0, 0), the recovery of Equation (26) indicates that the distribution is very broad, with median R=1 and a peak at R=0.

Figure 2A:
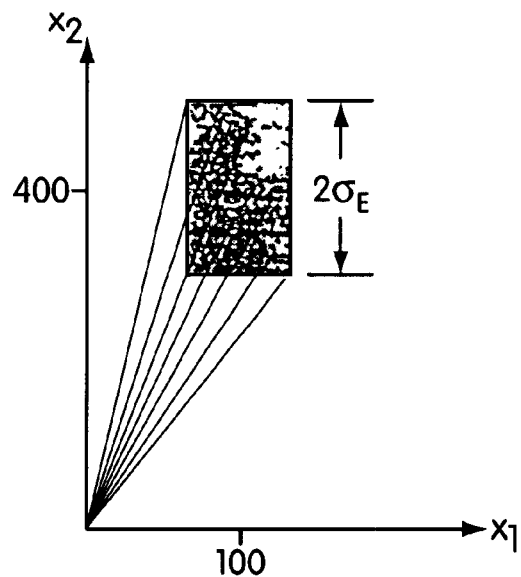
FIGS. 2, A and B, is a qualitative illustration of the derivation of Equation(16), explaining the behavior of the distributions shown in FIG. 1. For each pair of signals $(x_1, x_2)$, a box is drawn with extents $\pm\sigma_c$ about a point in the plane. Lines are drawn from the origin to the point in the box: the distribution of slopes of these lines is the a posteriori distribution of fold-changes. Panel A represents construction for signals (100, 400). Panel B represents construction for signals (5, 20).
Figure 2B:
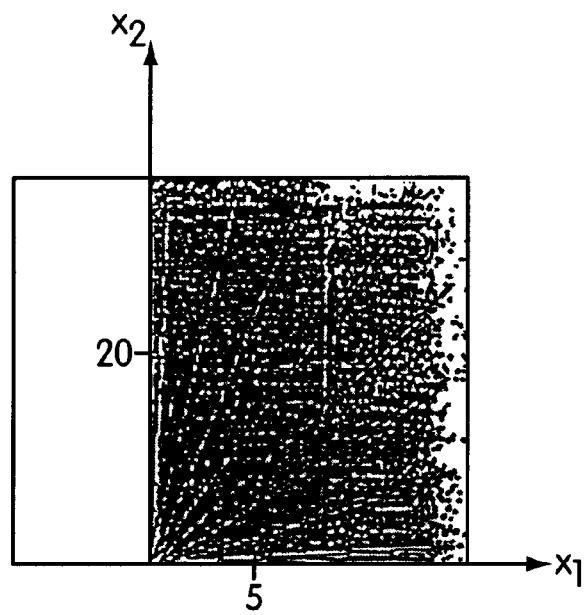

FIG. 2 qualitatively illustrates the behavior of the distribution $f_R(R)$, which was previously quantified in FIG. 1, through utilization of the following construction: (i) for each pair of values $(x_1, x_2)$, draw a box in the plane about the point $(x_1, x_2)$ with extents $\pm\sigma_\epsilon$ in each dimension, excluding regions which fall along negative axes and (ii) then draw a set of lines from the origin to all points in the box. The distribution of the slopes of these lines represents the a posteriori distribution $f_R(R)$.

4. Bayesian Estimation of Fold-Changes

Bayesian estimation of the fold-change R can be performed based on Equation (16) and knowledge of the measurements $x_1$ and $x_2$. Initially, the cumulative distribution function is defined:

$$F(R')=P(R \leq R')=\int_0^{R'} f_R(R)dR. \quad (29)$$

F(R) is preferably evaluated by use of numerical integration. Based upon the numerical values of F(R), the following information may be readily obtained.

4.1 Fold-change Estimator R:

The median estimator was chosen as an estimator R for the fold-change:

$$\bar{R}=\text{Med}(R), \quad (30)$$

that is, the value of R for which F(R)=1/2.

Other estimators are possible, for instance the MAP (Maximum a posteriori Probability) or the mean estimators. See e.g., Van Trees, H. L., *Detection, Estimation and Modulation Theory, Part I* (John Wiley and Sons), New York, 1998). However, the mean estimator is not used here, as $f_R(R)$ does not have a finite mean (i.e., it will always have a "tail" with dependence $1/R^2$, even in the near-normal limit of Equation(21)). Thus, the median estimator has the dual advantages of robustness and symmetry under the transformation ($R \rightarrow 1/R$), and is the one which is adopted herein. Formally, the median estimator is one that reduces, e.g., minimizes, the 25 absolute value of the (estimate-actual value) error term. See e.g., Van Trees, H. L., *Detection, Estimation and Modulation Theory, Part I* (John Wiley and Sons), New York, 1998).

4.2 Confidence Limits $R_p$ and $R_{1-p}$:

Given p<1, the confidence limits $R_p$ and $R_{1-p}$, are defined as the values of the corresponding percentiles:

$$F(R_p)=p, \quad (31)$$

$$F(R_{1p})=1-p. \quad (32)$$

4.3 P-value for Significance of Change:

The hypothesis R>1 ("a significant, positive fold-change occurred in experiment 2 relative to 1") may be tested by evaluating the probability of the complementary hypothesis, $R \leq 1$ and defining this as the P-value P of the hypothesis for significant change. This is simply represented as:

$$P=F(R=1). \quad (33)$$

Results for all the measurement pairs discussed in connection with FIG. 1 are also illustrated in FIG. 4 below, with confidence limits determined by p=0.16. Note that having the P-value provides a powerful selection criterion for retaining only those measurement pairs deemed significant. Thus, while all ratios of the measurements shown in FIG. 4 are equal to 4 (except of course for (0, 0)), only the first three entries ((100, 400), (50, 200), (25, 100)) are found to indicate a significant change (i.e., at the 0.05 confidence level). In turn, for each of these aforementioned tabular entries, confidence limits for the fold-change are known. Thus, for the measurement pair (25, 100), the estimate of R=3.6 is bracketed by the values (2.0, 8.8), showing that in this example the fold-change can not be ascertained more accurately than this reported interval (i.e., actual fold-changes as small as 2 and as large as 8.8 are consistent with the data).

5. Mapping Intensity Pairs $(x_1, x_2)$ into the (R, P) Plane

Figure 3:
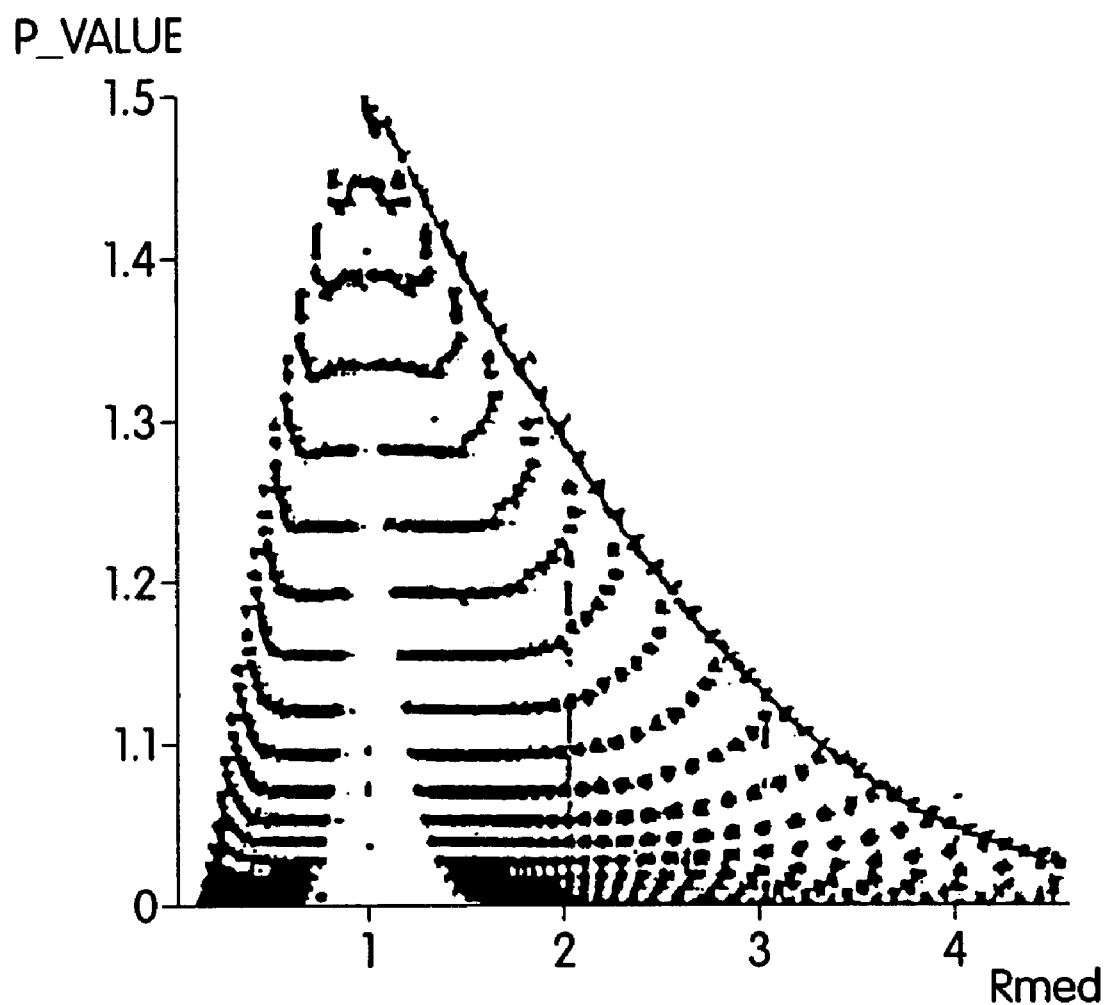
FIG. 3 is a graphical mapping of intensities $(x_1, x_2)$ into the (R, P) plane, as induced by Equations(30) and (33). Lines of constant $x_1$ and $x_2$ are shown. The dark line is the upper limit $P_u(R)$ of the range for P.

The pair of intensities $(x_1, x_2)$ are mapped by Equations (30) and (33) into pairs of numbers (R, P). This mapping, which provides a significance-weighted representation of the fold-changes, is illustrated in FIG. 3. For the sake of simplicity, $\sigma_1 = \sigma_2 \equiv \sigma$ was chosen.

FIG. 3 shows the lines of constant $x_1$ and constant $x_2$ in the (log(R), P) plane. The figure is symmetrical under the interchange $R \rightarrow (1/R)$ (i.e., $\log(R) \rightarrow -\log(R)$), because the value $\sigma_1 = \sigma_2$ was chosen for this particular example. For a given R, the range of P is finite, with an upper bound $P_u(R)$ such that:

$$0 \leq P \leq P_u(\bar{R}). \quad (34)$$

Because $P_u(R) \rightarrow 0$ as $R \rightarrow \infty$ or $R \rightarrow 0$, large fold-changes are necessarily correlated with small P-values, albeit always in a finite non-zero range.

An expression for $P_u(R)$ is given by: (see Equation (65) in Appendix A for a derivation of the term $P_u(R)$:

$$P_u(\bar{R}) = \begin{cases} \text{erfc}\left(t_m \frac{(\bar{R}^2 + \sigma_2^2/\sigma_1^2)^{1/2}}{(1+\sigma_2^2/\sigma_1^2)^{1/2}}\right), & \bar{R} \geq 1, \\ \text{erfc}\left(t_m \frac{(1/\bar{R}^2 + \sigma_1^2/\sigma_2^2)^{1/2}}{(1+\sigma_1^2/\sigma_2^2)^{1/2}}\right), & \bar{R} \geq 1, \end{cases} \quad (35)$$

where erfc is the complementary error function ((see Abramowitz, M. and Stegun, I. A., p. 297 *Handbook of Mathematical Functions* (Dover, N.Y., 1972)), and with $t_m \approx 0.477$. Equation(35) is strictly only asymptotically valid for R□1 or R■1, but in fact it provides an excellent approximation for all values of R, as can be seen in FIG. 3.

For R>1, the boundary $P=P_u(R)$ corresponds to the line $x_1=0$ in the $(x_1, x_2)$ plane (i.e., the $x_2$ axis). The points on this boundary are the points for which a given fold-change R has the least significance (i.e., has the largest value of P). Lines of constant R correspond to arcs within the $(x_1, x_2)$ plane, which all originate at the $x_2$ axis (for R>1), at which point P is a maximum, and which then asymptote to the line $x_2=Rx_1$, for which P rapidly tends to 0.

6. Implementation—The PFOLD Algorithm

The estimation scheme described hereinabove has been implemented in a C++ program called PFOLD. For a given set of input parameters $(x_1, x_2, \sigma_1, \sigma_2)$, specifying the two intensities and the corresponding standard deviations of the noise terms, PFOLD first numerically evaluates the distribution function $f\eta(R)$ (see Equation (16)) over a finite range $R_{min} \leq R \leq R_{max}$ at points on a regular mesh $R_i = R_{min} + i\Delta R$, i=0, 1, ... N, where $R_{min}$, $R_{max}$, and $\Delta R$ are automatically chosen to capture all of the variation of the function (FIG. 1). The cumulative distribution function F(R) (see Equation (29)) is then found by numerical integration of $f_R(R)$, following which all the estimators of Section 5 (i.e., the fold change R, the confidence limits $(R_p, R_{1-p})$, and the P-value P can be readily evaluated by numerically solving for Equations (30), (31), (32) and (33), respectively. In finding the roots of these aforementioned equations, a simple bisection method was used. See e.g., Press, W., et al., *Numerical Recipes in C, 2nd Edition*, p. 353 (Cambridge University Press, Cambridge, 1997).

7. Monte Carlo Simulations

A central problem in the analysis of expression data is separating significant from non-significant fold-change. In order to evaluate the usefulness of the statistics (R, P) in this process, a series of Monte Carlo simulations (see, e.g., Cowan, G., *Statistical Data Analysis*, p. 41 (Claredon Press, Oxford, 1998) were preformed which were aimed to approximate an actual experiment. Concentration values n were generated according to a log-normal distribution (see e.g., Cowan, G., *Statistical Data Analysis*, p. 34 (Claredon Press, Oxford, 1998), by computing:

$$n=\exp(y), \quad (36)$$

where y is a Gaussian random variable, generated with parameters:

$$\langle y \rangle = 7.25, \quad (37)$$

$$\sigma_y = 1.22, \quad (38)$$

where $\langle y \rangle$ and $\sigma_y$, are the mean and standard deviation of y, respectively. The parameters of Equations (37) and (38) result in a distribution with 25th percentile, median and 75th percentile with values:

$$n_{25} = 618, \quad (39)$$

$$n_{50} = 1408, \quad (40)$$

$$n_{75} = 3208, \quad (41)$$

respectively. The choice of a log-normal distribution for the concentration η is dictated by the empirical observation that in actual experiments, the distribution of intensities of present genes is approximately log-normal. For Affymetrix® chips, with an antibody staining procedure following hybridization, the intensities indicated by the percentiles in Equations (39), (40) and (41) are typical.

For each value of η generated by Equation (36), a real fold-change of b, combined with noise, was simulated by computing the two intensity values:

$$x_1 = n + \epsilon_1, \quad (42)$$

$$x_2 = bn + \epsilon_2, \quad (43)$$

where the noise terms $\epsilon_1$ and $\epsilon_2$ are uncorrelated Gaussian random variables with means $\langle\epsilon_1\rangle = \langle\epsilon_2\rangle = 0$, and with standard deviations given by Equation (6) with the parameters:

$$\sigma_C = 600, \alpha = 0.25. \quad (44)$$

Finally, from the intensities $(x_1, x_2)$ computed with Equations (42) and (43), the corresponding estimators (R, F) were computed using Equations (30) and (33).

7.1 Class Assignments:

In order to ascertain the degree of definiteness, two sets of simulations were conducted, each of which defined a class of genes undergoing a given fold-change:

Class 0: no change, b=1.

Class 1: change, b=3.

The effectiveness of using PFOLD to discriminate between the 2 classes of genes was evaluated to select genes which belong to Class 1. In order to accomplish this evaluation, an acceptance region D within the (R, F) plane was defined (see e.g., Cowan, G., *Statistical Data Analysis*, p. 47 (Claredon Press, Oxford, 1998), as well as defining the prediction π for the class membership of a gene to be:

$$\pi = \begin{cases} p \text{ if } (R^3, P)\epsilon D_1, \text{ (i.e. assign gene to class 1)} \\ \alpha \text{ if } (R^3, P)\epsilon D_1, \text{ (i.e. assign gene to class 0)} \end{cases} \quad (45)$$

where p and a stand for present and assent in the acceptance region, respectively. An example of an acceptance region D is one with a rectangular-decision surface defined by:

$$D = \{\vec{R} \geq R_c, P \leq P_c\}, \quad (46)$$

however, more general regions will be considered as well.

For any choice of D, it is possible to derive an estimate of the probabilities:

P(p|0)=probability that a gene in Class 0 gets assigned to Class 1,

P(a|0)=probability that a gene in Class 1 gets assigned to Class 0, by simply counting, in each case, the number of instances (R, P) which belong or, alternately, do not belong to D. If in turn, values are assumed for the a priori probabilities that, in a large set of genes, some will undergo no fold-change, and others a fold-change of 3 (for the sake of simplicity, it is assumed that no other fold-changes are possible outside of 1 or 3), $P_0$=a priori probability that a gene is in class 0, $P_1$=a priori probability that a gene is in class 1.

Bayes' theorem may then be utilized to obtain the a posteriori probabilities:

P(p|0)=probability that a gene assigned a significant fold-change did not really change, P(a|0)=probability that a gene assigned to the no-change category actually changed.

The result is:

$$P(0|p) = P_0 P(p|0)/P_p, \quad (47)$$

$$P(1|\alpha) = P_1 P(\alpha|1)/P_u. \quad (48)$$

where $P_p$ and $P_u$, the total a posteriori probabilities of declaring a gene in Class 1 or Class 0, respectively, are given by:

$$P_p = P(p|0)P_0 + (1 - P(\alpha|1))P_1, \quad (49)$$

$$P_0 = (1 - P(p|0))P_0 + P(\alpha|1)P_1. \quad (50)$$

The two quantities which are of greatest interest include:

$$P(a|1) = \text{absolute false negative rate}, \quad (51)$$

$$P(0|p) = \text{relative false positive rate}. \quad (52)$$

The definitions of Equations (51) and (52) are not symmetrical because the calculation of P(0|p) requires the value of the prior $P_1$, whereas the computation of P(a|1) does not. The absolute false negative rate is a measure of the fraction of all expressed genes that will be missed by the detection scheme at a given stringency. The relative false positive rate, on the other hand, refers to the fraction of the detected genes that is misclassified, and which did not in fact undergo a change. Therefore, the false negative rate, as defined herein, is thus a measure of the efficiency (see e.g., Cowan, G., *Statistical Data Analysis*, p. 47 (Claredon Press, Oxford, 1998), or sensitivity of the detection scheme (i.e., the smaller value is preferred), while the false positive rate is a measure of the purity (see e.g., Cowan, G., *Statistical Data Analysis*, p. 47 (Claredon Press, Oxford, 1998) or selectivity of the scheme (i.e., the smaller value is preferred).

Figure 6A:
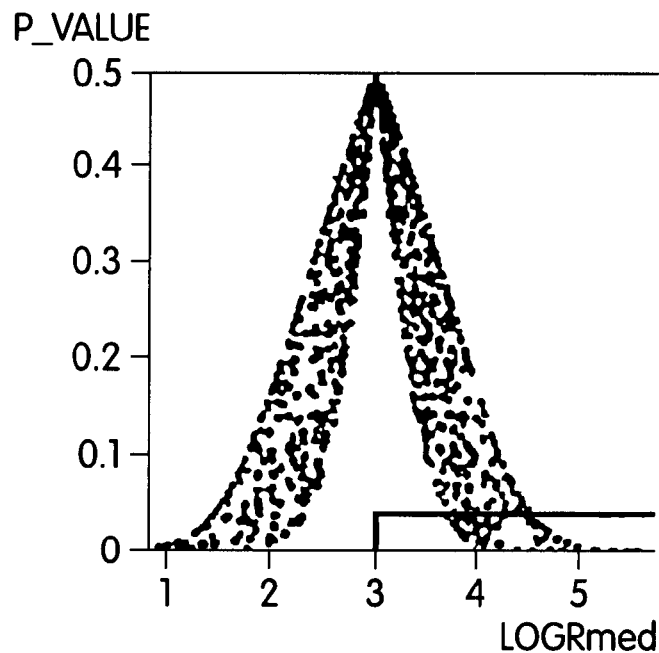
FIGS. 6, A and B, is a scatter of scatter plots in the (R, P) plane generated by: (1) 1000 genes from class 0, the no-change class (Panel A), and (2) 1000 genes from class 1 (Panel B).
Figure 6B:
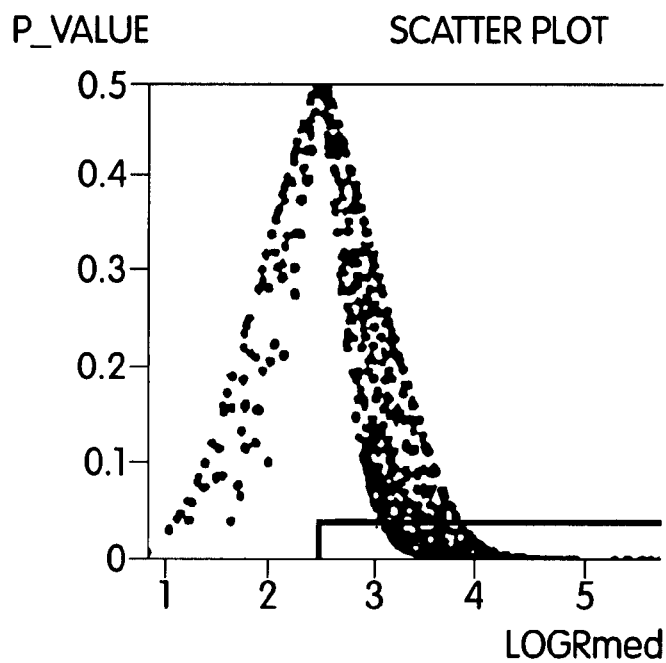

7.2 Results of Experimental Simulation:

In FIG. 6 (Panels A and B), there is a comparison of scatter plots within the (R, P) plane generated by 1000 genes from Class 0 (the no-change class) and 1000 genes in Class 1 (the genes which exhibited a 3-fold change), respectively. In order to facilitate understanding of this concept, the following equations are based upon a scenario with an a priori probability of a gene changing of:

$$P_i = 0.2. \quad (53)$$

This defines a configuration with 1000 genes changing 3-fold, against a background of 4000 unchanging genes.

A method of choice for displaying the dependence of error rates on the position of a decision surface is the construction, in graphical format, of the so-called receiver operating characteristic (ROC) of the decision scheme. See e.g., Van Trees, H. L., *Detection, Estimation and Modulation Theory, Part I* (John Wiley and Sons), New York, 1998). The ROC enables one to clearly visualize the tradeoff between reducing, e.g., minimizing, false positive rates, thereby increasing the selectivity of the scheme, and reducing, e.g., minimizing, false negative rates, thereby also increasing the overall sensitivity of the given scheme.

Figure 7:
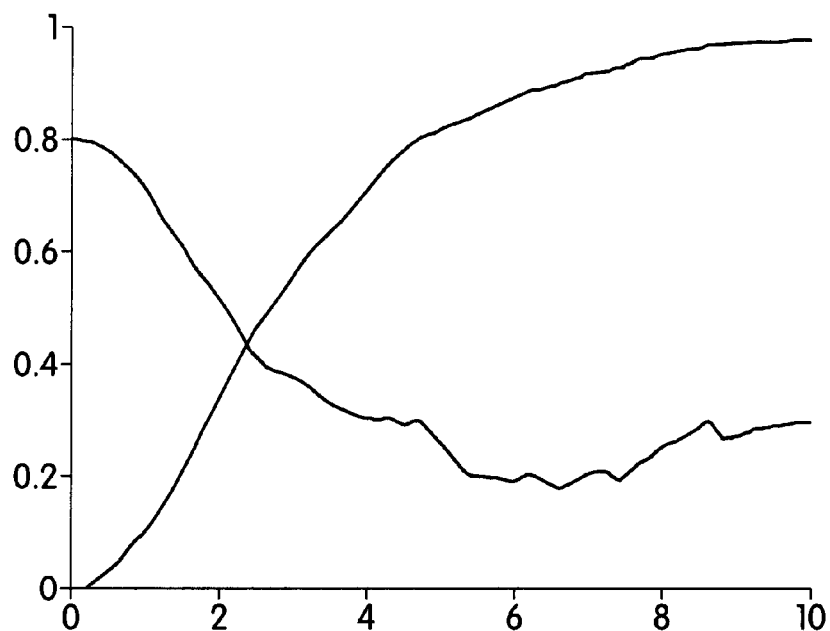
FIG. 7 is a line graph depicting a receiver operating characteristic (ROC) for the statistic t=P.
Figure 8:
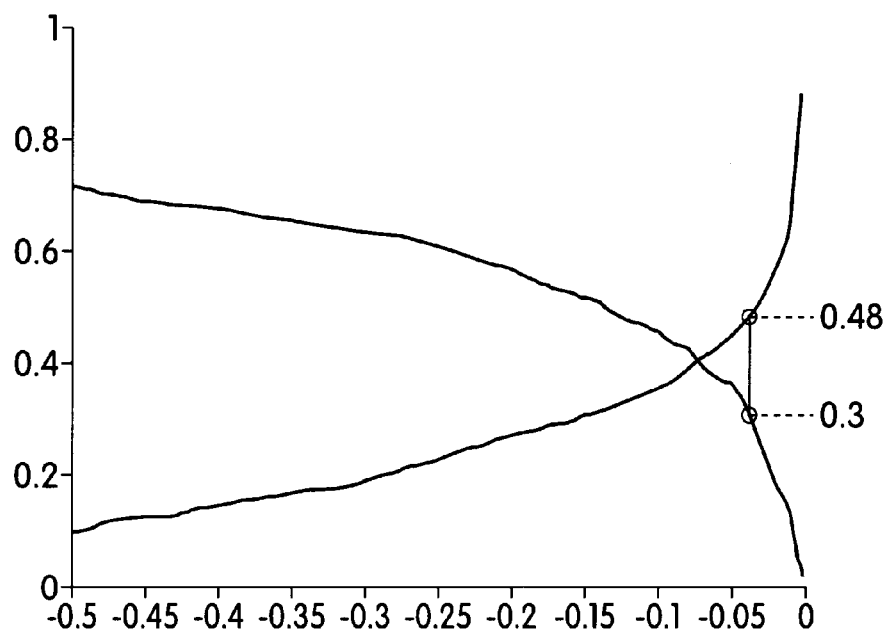
FIG. 8 is a line graph depicting a receiver operating characteristic (ROC) for the statistic t=−P.

In FIG. 7, the receiver operating characteristic (ROC) are plotted which are obtained when one use as statistic for a decision boundary the fold-change itself, t=R. Thus, in the previous case, the acceptance region is defined simply as:

$$D=\{\vec{R} \geq R_c\}. \tag{54}$$

so that the decision surface is a vertical line within the (R, P) plane. In FIG. 7, the false positive rate P(0|p) and the false negative rate P(a|1) are plotted as a function of $R_c$. It can be seen that as the stringency of the test for acceptance is increased (i.e., increasing $R_c$), the relative false-positive rate decreases (i.e., the purity of the detected sample increases), but that there is also a concomitant increase in the absolute false negative rate as well. In addition, FIG. 8 illustrates the receiver operating characteristic (ROC) which is obtained for the statistic t=–P.

Figure 9:
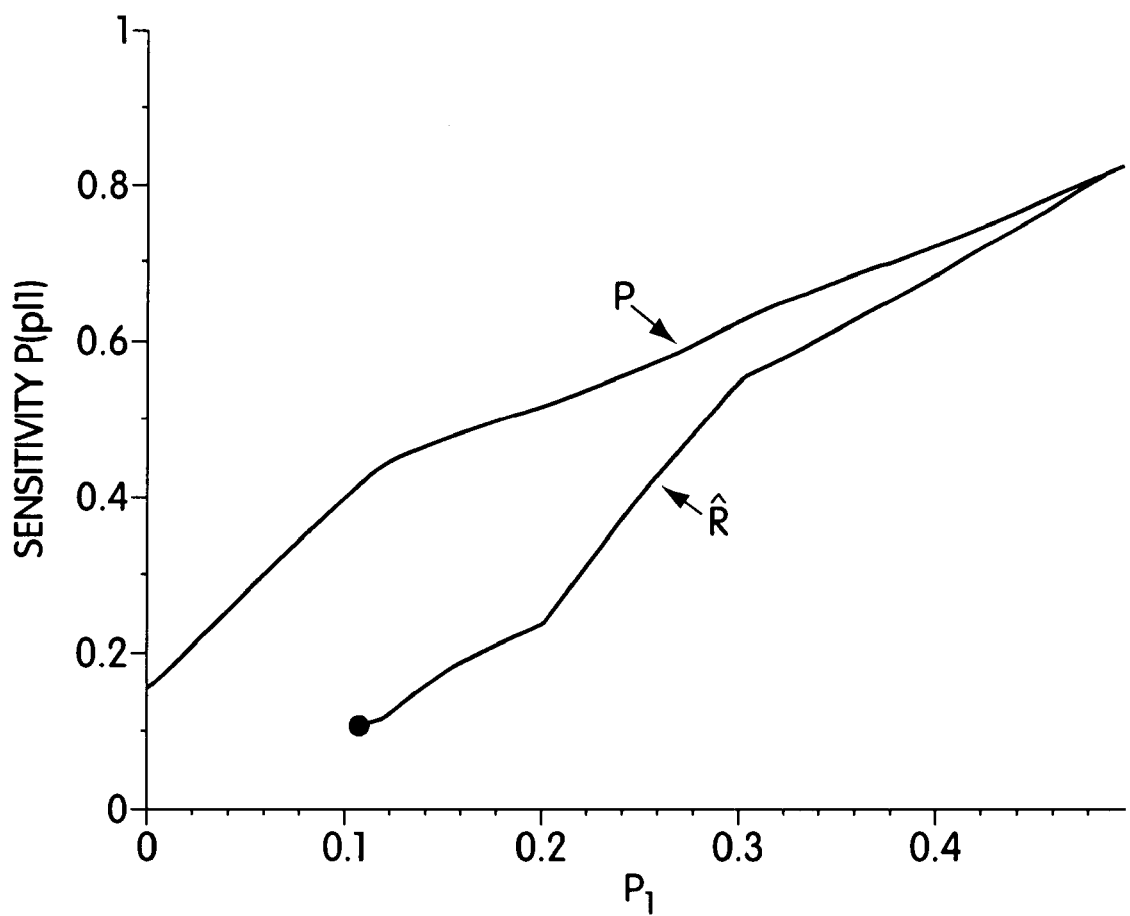
FIG. 9 is a line graph illustrating the compared sensitivity as a function of $P_1$=fraction of genes which underwent a change (b=3), for the R and P statistics. A fixed relative false positive rate P(0|p)=0.3 is imposed throughout.

FIG. 5 illustrates in tabular form the performance of the three statistical methodologies utilized for the detection of 1000 genes with actual fold-change of b=3, against a background of 4000 genes with no fold-change of b=1, based upon the Monte Carlo experimental simulations described in Section. 7 (i.e., the a priori probability of a gene undergoing the 3-fold change is $P_1$=0.2). Specific results are reported for a fixed false positive rate P(0|p)=0.3. FIG. 9 illustrates the compared sensitivity as a function of $P_1$=fraction of genes which underwent a change (b=3), for the R and P statistics. A fixed relative false positive rate P(0|p)=0.3 is imposed throughout.

The results illustrated in FIG. 5 and FIG. 7 show that the use of the P-value (t=–t statistic) instead of, or in conjunction with, the fold-change R, can markedly increase the sensitivity of the various ranges of parameters which were, heretofore, extremely hard to detect.

In conclusion, due to the low signal-to-noise ratio which is inherent in expression data, this noise must be carefully accounted for. The PFOLD algorithm disclosed herein offers a theoretical and practical framework for dealing with noise. For example, the PFOLD algorithm allows for two important metrics for fold-change of the level of gene expression: (i) the P-value, which reflects the overall "quality" of the ratio; and (ii) R, which reflects the "quantity" of the fold-change in the expression of the gene(s). In addition, the PFOLD p-statistic is essential for quantifying small populations of changing genes and/or small fold-changes of the expression level of such genes.

APPENDIX A: DISTRIBUTION FOR $X_1$=0

For a given fold-change R>1, the least significant predictions arise from an intensity pair with $x_1$=0. To investigate this dependency, the approximate form of Equation (16) is generated when $x_1$=0, and $x_2$>>$\sigma_{1,2}$. The result is:

$$f_R(R) \approx \left(\frac{2}{\pi}\right)^{1/2} \frac{Ry}{(R^2+\sigma_2^2/\sigma_1^2)^{3/2}} \exp\left(-\frac{y^2}{2(R^2+\sigma_2^2/\sigma_1^2)}\right), \tag{55}$$

where y=$x_2/\sigma_1$. With the transformation:

$$u = \frac{1}{(R^2+\sigma_2^2/\sigma_1^2)^{1/2}}, \tag{56}$$

the interval $0 \leq R < \infty$ is mapped into $0 < u < \sigma_1/\sigma_2$, and the distribution for u is given by:

$$f_u(u) = \left(\frac{2}{\pi}\right)^{1/2} y \exp(-y^2 u^2/2). \tag{57}$$

It is easy to check that the correct normalization of the distribution function obtains, since:

$$\int_0^\infty f_R(R) dR = \int_0^{\sigma_1/\sigma_2} f_u(u) du \approx \int_0^\infty f_u(u) du = 1. \tag{58}$$

The approximation in Equation (58) holds because y=$x_2/\sigma_1$>>1.

To compute the P-value for a given value of y:

$$P = P(R \leq 1) = P(u \geq u_1), \tag{59}$$

where:

$$u_1 = (1+\sigma_2^2/\sigma_1^2)^{1/2}. \tag{60}$$

Using Equation (57), and integrating over the range $u_1 \leq u < \infty$, it is found that:

$$P = \text{erfc}\left(\frac{y}{2^{1/2}}(1+\sigma_2^2/\sigma_1^2)^{-1/2}\right). \tag{61}$$

To compute the predicted fold change R for a given value of y, the definition of R as the median of the distribution is utilized:

$$1/2 = P(R \leq \vec{R}) = P(u \geq). \tag{62}$$

This results in the equation:

$$\frac{1}{2} = \text{erf}\left(\frac{y}{2^{1/2}}(\vec{R}^2+\sigma_2^2/\sigma_1^2)^{-1/2}\right), \tag{63}$$

from which we find the relation between y and R:

$$y = 2^{1/2} t_M (\vec{R}^2 + \sigma_2^2/\sigma_1^2)^{1/2}. \tag{64}$$

where $t_M \approx 0.477$ is the root of the equation erf($t_M$)=1/2. Using Equation (64), y can be eliminated from Equation (61), obtaining the final equation:

$$P_u(\vec{R}) = \begin{cases} \text{erfc}\left(t_m \frac{(\vec{R}^2+\sigma_2^2/\sigma_1^2)^{1/2}}{(1+\sigma_2^2/\sigma_1^2)^{1/2}}\right), & \vec{R} \geq 1, \\ \text{erfc}\left(t_m \frac{(1/\vec{R}^2+\sigma_1^2/\sigma_2^2)^{1/2}}{(1+\sigma_1^2/\sigma_2^2)^{1/2}}\right), & \vec{R} \geq 1, \end{cases} \tag{65}$$

where $t_M \approx 0.477$.

Figure 11:
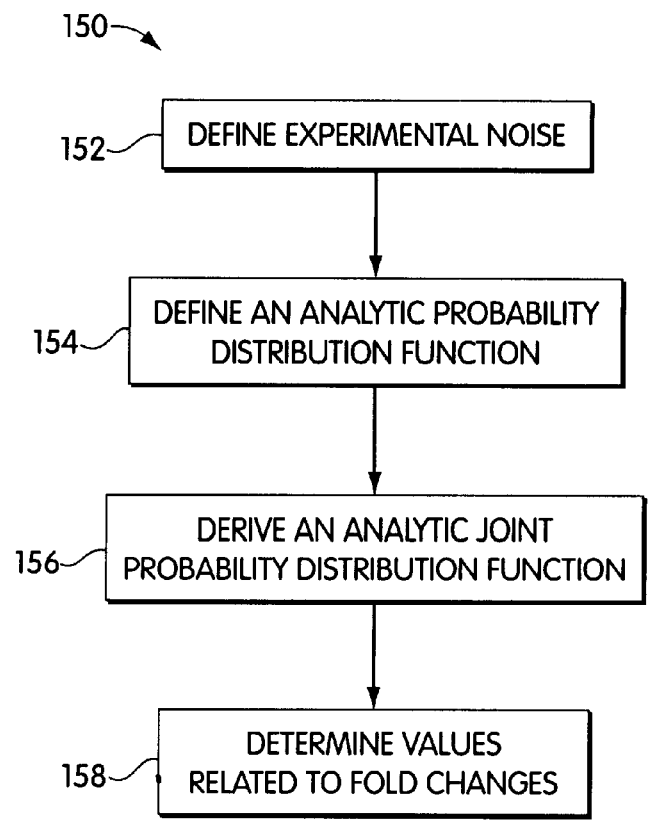
FIG. 11 is a flow diagram of a process according to the invention.

Referring to FIG. 11, a process 150 for calculating differences in the level of gene expression in at least one array of genes is shown. The process 150 uses a mathematical formula to describe an a posteriori statistical distribution of the levels (e.g., all the levels) of gene expression that may be derived from the measurements obtained of levels of gene expression in one or more cells or tissue types represented in the at least one array.

At stage 152, an experimental noise associated with intensity of hybridization signal for each gene in the at least one array is defined. This noise is experimental noise, being variations in observed levels on chips or other microarrays rather than biological noise, which is the variation of expression level seen in biological systems.

At stage 154, the defined experimental noise is used to define an analytical probability distribution function (pdf) describing distribution values of intensity for each gene. The noise is assumed to be Gaussian and the analytical pdf is defined using Bayes Theorem. The analytic pdf is a continuous function.

At stage 156, the analytic pdfs are used to derive an analytical joint pdf describing possible ratios or fold changes for differentially-expressed genes or gene products in the at least one array. The analytical joint pdf describing possible ratios or fold changes may be derived for any differentially-expressed genes or gene products.

At stage 158, the joint pdfs are applied, using experimentally-derived intensities and noise values from the genes on the at least one array, to determine values related to fold changes associated with the genes. The fold changes in the concentration of gene transcripts are estimated. The confidence limits on the fold change given specific confidence intervals are established. A p-value, or quality metric associated with the fold change estimate is also derived. This value represents the probability that a fold change could be less than 1 when the estimate is greater than 1, or the probability that the fold change is greater than 1 when the estimate is less than 1.

The estimated fold change represents the difference in level of gene expression observed. The total variance (noise) may still be high even as the concentration of transcript goes to zero.

EQUIVALENTS

From the foregoing detailed description of the specific embodiments of the invention, a unique mathematically-derived a posteriori distribution for the estimation of alterations in gene expression has been described. Although particular embodiments have been disclosed herein in detail, this has been done by way of example for purposes of illustration only, and is not intended to be limiting with respect to the scope of the appended claims which follow. In particular, it is contemplated that various substitutions, alterations, and modifications will become apparent to those skilled within the art from the foregoing description and accompanying figures and may be made to the invention without departing from the spirit and scope of the invention as defined by the claims. Such modifications are intended to fall within the scope of the appended claims.

Also, due to the nature of software, functions described above can be implemented using software, hardware, firmware, hardwiring, or combinations of any of these. Items implementing functions may also be physically located at various positions, including being distributed such that portions of functions are implemented at different physical locations.

What is claimed is:

1. A method for calculating indicia of differences in gene-expression level in a plurality of array hybridizations, the method comprising:
   (a) determining an indication of experimental noise associated with intensity of hybridization signal for a gene on each array hybridization;
   (b) using the determined experimental noise indication to determine a first analytical probability distribution function describing distribution values of intensity for the gene on each array hybridization, assuming the noise is Gaussian and by applying Bayes Theorem;
   (c) using the first analytic probability distribution functions to derive a second analytical probability distribution function describing an indication of a gene-expression difference of a differentially-expressed gene; and
   (d) applying the second probability distribution function of the differentially-expressed gene using experimentally-derived intensities and noise values from the array hybridizations to determine values related to the gene-expression difference.

2. The method of claim 1 wherein the determined values include estimated fold changes in the concentration of gene transcripts.

3. The method of claim 2 wherein the determined values include a quality metric associated with at least one of the estimated fold changes.

4. The method of claim 3 wherein the quality metric represents at least one of a probability that a fold change could be less than 1 when an estimated fold change is greater than 1, and a probability that a fold change is greater than 1 when the estimated fold change is less than 1.

5. The method of claim 1 wherein the determined values include confidence limits on the fold change given specific confidence intervals.

6. A computer program product, for calculating indicia of differences gene-expression level in a plurality of array hybridizations, residing on a computer-readable medium and comprising instructions for causing a computer to:
   (a) determine an indication of experimental noise associated with intensity of hybridization signal for a gene on each array hybridization;
   (b) use the determined experimental noise indication to determine a first analytical probability distribution function describing distribution values of intensity for the gene on each array hybridization, assuming the noise is Gaussian and by applying Bayes Theorem;
   (c) use the first analytic probability distribution functions to derive a second analytical probability distribution function describing an indication of a gene-expression difference of a differentially-expressed gene;
   (d) apply the second probability distribution function of the differentially-expressed gene using experimentally-derived intensities and noise values from the array hybridizations to determine values related to the gene-expression difference.

7. The computer program product of claim 6 wherein the determined values include estimated fold changes in the concentration of gene transcripts.

8. The computer program product of claim 7 wherein the determined values include a quality metric associated with at least one of the estimated fold changes.

9. The computer program product of claim 8 wherein the quality metric represents at least one of a probability that a fold change could be less than 1 when an estimated fold change is greater than 1, and a probability that a fold change is greater than 1 when the estimated fold change is less than 1.

10. The computer program product of claim 6 wherein the determined values include confidence limits on the fold change given specific confidence intervals.

11. The method of claim 1 wherein an indication of experimental noise is determined, the first probability distribution function is determined, and the second probability distribution function is derived and applied for each gene on each array hybridization.

12. The computer program product of claim 6 wherein the instructions for causing a computer to determine an indication of experimental noise, determine the first probability distribution function, derive the second probability distribution function, and apply the second probability distribution function, cause the computer to do so for each gene on each array hybridization.

* * * * *

UNITED STATES PATENT AND TRADEMARK OFFICE
CERTIFICATE OF CORRECTION

PATENT NO. : 6,502,039 B1
DATED : December 31, 2002
INVENTOR(S) : Theilhaber et al.

It is certified that error appears in the above-identified patent and that said Letters Patent is hereby corrected as shown below:

<u>Title page, Item [60] and Column 1, line 7,</u>
Related U.S. Application Data, "filed on May 25, 2000" should read
-- filed on May 25, 1999 --.

Signed and Sealed this

Twenty-third Day of March, 2004

JON W. DUDAS
*Acting Director of the United States Patent and Trademark Office*